United States Patent [19]

Suggs

[11] 4,241,206

[45] Dec. 23, 1980

[54] KETONE SYNTHESIS BY HYDROACYLATION

[75] Inventor: John W. Suggs, Watchung, N.J.

[73] Assignee: Bell Telephone Laboratories, Incorporated, Murray Hill, N.J.

[21] Appl. No.: 955,309

[22] Filed: Oct. 27, 1978

[51] Int. Cl.$^3$ .................... C07C 45/61; C09B 23/00;

[52] U.S. Cl. .................... 542/424; 542/406; 546/304; 546/311; 546/307; 568/312; R; 568/317; 568/386

[58] Field of Search ............... 260/597 R, 580 R, 592, 260/566 R; 546/304, 311, 307; 542/406, 424

[56] References Cited

U.S. PATENT DOCUMENTS

| | | | |
|---|---|---|---|
| 2,974,172 | 3/1961 | Luvisi | 260/566 R |
| 3,230,216 | 1/1966 | Stork | 260/566 R |
| 3,422,142 | 1/1969 | Zueck | 260/566 R |
| 3,591,598 | 7/1971 | Traise et al. | 546/304 |
| 3,686,262 | 8/1972 | Groen | 260/566 R |

FOREIGN PATENT DOCUMENTS 2166941 5/1977 Fed. Rep. of Germany ...... 260/593 R

OTHER PUBLICATIONS

Kos'minykk et al., Chem. Abst., vol. 79, p. 435, #31800 c, (1973).

Martirosyan et al., Chem. Abst., vol. 78, p. 451, #43046 x, (1973).

Saskyan et al., Chem. Abst., vol. 85, #46042y, (1974).

Martirosyan et al., Chem. Abst., vol. 79, p. 323, #136399a, (1973).

*Primary Examiner*—James H. Reamer
*Attorney, Agent, or Firm*—Peter V. D. Wilde

[57] ABSTRACT

The invention is a generalized hydroacylation reaction. The reaction involves the activation of a selected aldehyde by converting by iminization to an aldimine or an aminal. The imine group replaces the carbonyl group. The imine C-H bond is then susceptible to attack by a chosen olefin, and hydrolysis to yield the ketone. One moiety of the ketone derives from the aldehyde and the other from the olefin added later. Therefore, the ketone may be symmetrical or unsymmetrical. Both aromatic and aliphatic aldehydes may be activated according to this process.

9 Claims, No Drawings

KETONE SYNTHESIS BY HYDROACYLATION

BACKGROUND OF THE INVENTION

Hydrocarbonylation has become an important and versatile approach to the synthesis of organic compounds and is commercially important for the synthesis of aldehydes. The reaction is based on the old OXO reaction which is the addition of a carbonyl group at an unsaturated bond in an olefin.

The most important industrial hydrocarbonylation reaction is hydroformylation which is the addition of formaldehyde to an olefin, resulting typically in an aldehyde. This reaction has been studied widely, and is regarded as a generalized procedure for aldehyde synthesis. Although hydroformylation can proceed stoichiometrically, the favored commerical reaction if catalytic.

Carbonylation reactions appear to be attractive for ketone synthesis, but the hydroformylation reaction fails for generalized ketone synthesis. In exceptional cases, ketones can be formed either stoichiometrically or catalytically by hydroformylation. Diethyl ketone forms readily by carbonylation of ethylene, although it competes in yield with propionaldehyde. Dibutyl ketone can be synthesized by carbonylation, though not as effectively. Other ketone synthesis reactions are rare or very specialized. Those that exist, it will be noted, form symmetrical ketones.

The catalysts used in hydroformylation reactions are normally cobalt or rhodium compounds although a host of metal complexes have been used. Rhodium catalysts are the newest, and are often the most selective for a preferred end product.

Nearly all the significant carbonylation reactions to date have involved hydroformylation. Although, in principle, higher order carbonylation, i.e., hydroacylation, appears an attractive possibility, efforts to obtain that reaction have been largely unsuccessful, and in particular, a general synthesis of unsymmetrical ketones by a carbonylation route which is catalytic in a metal compound has not been reported.

SUMMARY OF THE INVENTION

I have discovered a generalized hydroacylation reaction for the production of symmetric or asymmetric ketones. The reaction involves the activation of a selected aldehyde through conversion by iminization to an aldimine or an amimal. The imine group replaces the carbonyl group. The imine C-H bond is then susceptible to attack by a chosen olefin, under the influence of a metal catalyst, followed by hydrolysis to yield the ketone. One moiety of the ketone derives from the aldehyde and the other from the olefin added later. Thus the ketone may be symmetrical or unsymmetrical. Both aromatic and aliphatic aldehydes may be activated according to this process. To date, we have not succeeded in adding aromatic moieties to the activated species. However, moieties containing aromatic structures with olefin groups, such as benzylidyne and cinnamylidene compounds, are regarded as equivalent to the simple olefins in the context here. Likewise, we have had success only with 1-olefins. It may be that other reaction conditions will allow adding a greater variety of moieties, and we do not regard this as a necessary limitation of the process.

DETAILED DESCRIPTION

The activation of the aldehyde proceeds according to the invention by the following general reaction:

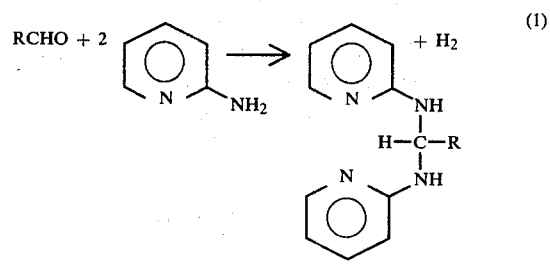
(1)

The animal thus formed dissociates at moderate temperatures:

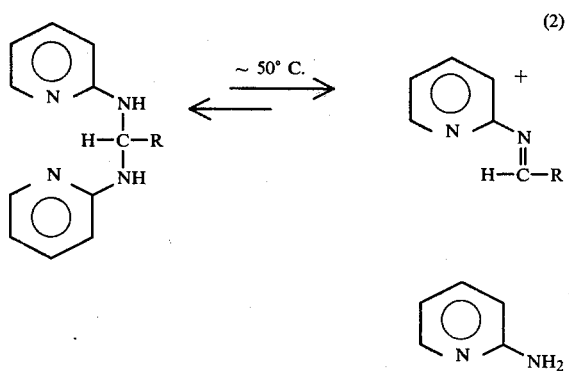
(2)

The imine thus formed is the species of interest. It is then complexed with a conventional rhodium catalyst which activates the imine C-H group for acylation with a chosen olefin group:

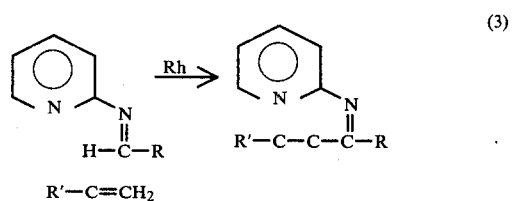
(3)

thus producing a 2-aminopyridylketamine which by hydrolysis yields the ketone:

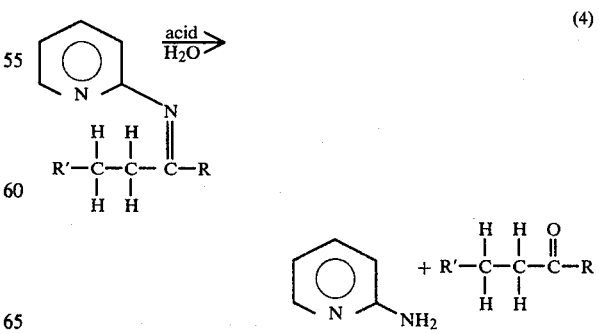
(4)

The selection of the aldehyde for this hydroacylation sequence appears to have no limitations. The important group for the iminization step is theorized to be a tertiary nitrogen bridged to a primary nitrogen through a single atom preferably through a resonant ring structure. Thus, the selection of 2-amino pyridine compounds. Substituents at the 4, 5, and 6 positions appear not to hinder the reaction and therefore can be introduced at will. Substitutions at the three position do effect the reaction. Thus for example, 3-methyl-2-amino pyridine appears to react satisfactorily only with aromatic aldehydes to form the imine directly:

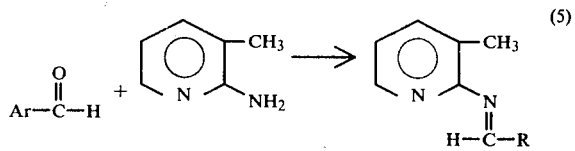 (5)

The presence of the substituent in the three position hinders the formation of the aminal. In a sense this is a more direct route to the desired product and in fact was the first successful hydroacylation reaction I observed. It was later realized that aminal formation leads also to the desired objective because the imine (or aldimine) is an equilibrium product, though in small amounts, with the aminal (see reaction 2). The fact that the equilibrium is strongly toward the aminal is unimportant in the presence of the rhodium catalyst because depletion of the imine as it is formed by reaction with the rhodium compound drives the equilibrium favorably. Equivalent results for substituents other than methyl in the three position would be expected. Higher order alkyl groups, nitro, amino and halogen substituents would be included among these. Similar substituents in the 4, 5 and 6 positions could be used.

For aldehydes having an alpha hydrogen formation of the aminal intermediate is preferred. Accordingly, if the aldehyde group is attached to an alkyl group or a saturated ring, reaction (1) proceeds more effectively than reaction (5). This appears to happen because the imine formed with an alpha hydrogen prefers to react with itself to form large molecules with repeating units, rather than to react with the hindered pyridine compound to form the aminal.

The rhodium derivatives useful as carbonylation catalysts are well known. See Wender, *Organic Synthesis via Metal Carbonyls* Vol. 2, pp. 136 et seq. (1977). The generalized formula for the main class of these is:

$$RhX(PR_3)_3$$

where X is anionic and selected from the group typically of halide, cyanide, alkoxide, thiolate, etc., and R is alkyl, aryl, alkoxy, aryloxy, etc. Other rhodium compound catalysts are known such as rhodium oxide, rhodium halide, rhodium nitrate, rhodium carbonyls and even rhodium complexed with polymers. Rhodium metal coated onto inert carriers such as alumina have also been used. A known advantage of rhodium catalysts is that conditions for a given reaction have a small dependence on the particular rhodium compound chosen. Therefore the various known compounds are regarded in the art as highly interchangeable. Rhodium catalysts are also known to be more selective and also to require milder reaction conditions than, e.g., cobalt catalysts.

The following specific embodiments are given as illustrative of the hydroformylation technique.

1. General Procedure for the Preparation of Aldimines from 3-methyl-2-aminopyridine and Aromatic Aldehydes. The 3-methyl-2aminopyridyl Aldimine of Benzaldehyde.

Into a 100 ml round bottom flask was placed 5 g. of 3-methyl-2-aminopyridine and 5 g. of freshly distilled benzaldehyde. 50 ml of tetrahydrofuran was the solvent. Water was removed as formed by the presence of 10 g. of 4A molecular sieves. The solution was heated at reflux with protection from atmospheric moisture for 3 days, whereupon the solution was filtered to remove the molecular sieves and solvent removed at reduced pressure on a rotary evaporator. The residual yellow oil was distilled using a short vigeraux column at reduced pressure to give 7.79 g. (85% yield) of the 3-methyl-2-aminopyridyl aldimine of benzaldehyde, as a pale yellow oil, BP 100 degrees at 0.1 mm. The reaction is represented by equation (5).

2. General Procedure for the Preparation of 2-aminopyridyl Aminals from 2-aminopyridine and aliphatic Aldehydes. The 2-aminopyridyl Aminal of Cyclohexanecarboxaldehyde.

2-aminopyridine, 2.30 g., and cyclohexanecarboxaldehyde, 1.37 g., were dissolved in 10 ml of $CH_2Cl_2$ containing 2 g. of 4A molecular sieves. After stirring overnight with a magnetic stirrer, the solution was filled with a white solid. This solid was dissolved in 100 ml of hot tetrahydrofuran and filtered to remove the molecular sieves. Solvent removal on a rotary evaporation gave 3.0 g. (88%) of the 2-aminopyridyl aminal of cyclohexanecarboxaldehyde, M.P. 124–125.5 degrees after recrystallization from benzene. The reaction is represented by equation (2).

3. Catalytic Hydroacylation of Ethylene Using 3-methyl-2-aminopyridyl Aldimines and Tristriphenylphosphinorhodium (1) Chloride.

Into a stainless steel autoclave with a glass liner was placed 1.5 g. of the 3-methyl-2-aminopyridyl aldimine of benzaldehyde, 75 ml of tetrahydrofuran and 0.2 g. of $RhCl(PPh_3)_3$. The autoclave was flushed with ethylene, to remove any air, then pressurized with ethylene to 150 psi, followed by heating to 180 degrees C. for 14 hours. Upon cooling the resulting dark red liquid was concentrated to one-fourth its original volume and stirred with moist silica gel in 20 ml of $CH_2Cl_2$ for 1 hour. Solvent was removed on the rotary evaporator and the product propiophenone was obtained by heating the silica gel at 130 degrees and 50 mm and collecting the distillate. The yield of propiophenone, as a clear oil, was 0.45 g., 45% yield based on starting aldimine and 1800% yield based on the rhodium catalyst.

4. Catalytic Hydroacylation of Ethylene Using the 2-aminopyridyl Aminal of Cyclohexanecarboxaldehyde and Tris-triphenylphosphinorhodium (1) chloride.

The reaction conditions in example 3 were followed, using 0.85 g. of the 2-aminopyridyl aminal of cyclohexanecarboxaldehyde and 0.10 g. of $RhCl(PPh_3)_3$ in 30 ml of tetrahydrofuran, except the initial ethylene pressure was 600 psi. Workup of the product mixture as above gave 0.28 g., 66% yield based on starting aminal, of ethyl cyclohexyl ketone.

5. Catalytic Hydroacylation of 1-Octene with the 2-aminopyridyl Aminal of Decyl Aldehyde and $RhCl(PPh_3)_3$.

In a 500 ml poly(tetrafluoroethylene) lined autoclave was placed 0.05 g. of $RhCl(PPh_3)_3$, 50 ml of toluene and 3 g. of 1-octene. The autoclave was flushed with argon and heated to 160 degrees C. for 12 hours. Upon cooling the solvent was removed on a rotary evaporator and the red residue treated with moist silica gel in dichloromethane for 2 hrs. to hydrolyze all the Schiff base to produce ketone. Extraction of the silica gel with $CH_2Cl_2$ and column chromatography (on 60 g. of silica gel, elutant hexane -2% ether) gave the desired 9-octadecanone, 0.12 g., 10% yield, 850% based on $RhCl(PPh_3)_3$. Less than 5% of the branched chain ketone, 7-methyl-9-heptadecanone, was formed.

6. Catalytic Hydroacylation of 1-octene with the 2-aminopyridyl Aminal of Decyl Aldehyde and $RhBr(PPh_3)_3$.

Example 5 was repeated using $RhBr(PPh_3)_3$ as the catalyst. The expected product, 9-octadecanone, was obtained as before in 10% yield.

7. Catalytic Hydroacylation of Ethylene using the 2-aminopyridyl Aminal of Cyclohexanecarboxaldehyde and Tris-tri(4-methylphenyl)phosphinorhodium (1) chloride.

Example 4 was repeated using 0.10 g. of tris-tri(4-methylphenyl) phosphinorhodium (1) chloride as the catalyst. Ethyl cyclohexyl ketone was isolated as above, 0.26 g.

I claim:

1. A method for the production of a ketone comprising the steps of:

a. reacting an aldehyde of the formula:

where $R_1$ is alkyl or aryl, with a heterocyclic compound of the formula:

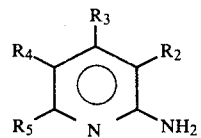

where $R_2$, $R_3$, $R_4$, and $R_5$ are selected from hydrogen, alkyl, nitro, amino and halogen when $R_1$ is alkyl, and $R_2$ is selected from alkyl, nitro, amino and halogen, and $R_3$, $R_4$, and $R_5$ are selected from hydrogen, alkyl, nitro, amino and halogen when $R_1$ is aryl, thus forming a reaction product of the formula:

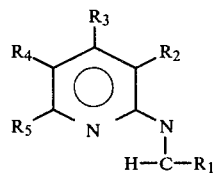

b. combining this reaction product with an olefin of the formula:

where $R_6$ is alkyl or aryl, in the presence of a rhodium catalyst selected from the group consisting of rhodium oxide, rhodium halide, rhodium nitrate, rhodium carbonyl, polymers containing rhodium and

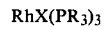

where X is anionic and selected from the group consisting of halide, cyanide, alkoxide, and thiolate, and R is selected from the group consisting of alkyl, aryl, alkoxy and aryloxy, and c. hydrolyzing to form a ketone having the formula:

2. A method for producing a 2-aminopyridylketamine comprising:

reacting an olefin of the formula:

where $R_1$ is alkyl or aryl, with an imine compound of the formula:

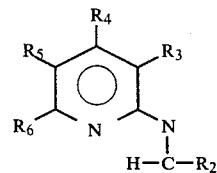

where $R_2$ is alkyl or aryl and $R_3$, $R_4$, $R_5$, and $R_6$ are hydrogen, alkyl, nitro, amino or halogen, and a catalyst selected from the group consisting of rhodium oxide, rhodium halide, rhodium nitrate, rhodium carbonyl, polymers containing rhodium and

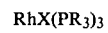

where X is anionic and selected from the group consisting of halide, cyanide, alkoxide, and thiolate, and R is selected from the group consisting of alkyl, aryl, alkoxy and aryloxy, to form a product with the formula:

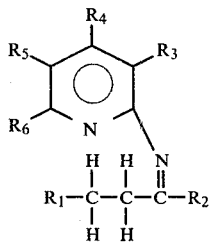

3. The method of claims 1 or 2 in which the rhodium catalyst is

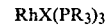

where X is anionic and selected from the group consisting of halide, cyanide, alkoxide, and thiolate, and R is selected from the group consisting of alkyl, aryl, alkoxy and aryloxy.

4. The method of claim 1 in which the aldehyde is an aliphatic aldehyde.

5. The method of claim 1 in which the aldehyde is a cyclic aldehyde.

6. The method of claim 1 in which the aldehyde is an aromatic aldehyde.

7. The method of claim 1 in which the olefin is a 1-olefin.

8. The method of claim 1 in which the $R_2$ is alkyl and the aldehyde has no alpha hydrogen.

9. The method of claim 8 in which $R_2$ is a methyl group.

* * * * *

UNITED STATES PATENT AND TRADEMARK OFFICE
CERTIFICATE OF CORRECTION

PATENT NO. : 4,241,206
DATED : December 23, 1980
INVENTOR(S) : John W. Suggs

It is certified that error appears in the above—identified patent and that said Letters Patent is hereby corrected as shown below:

Column 1, line 18, "if" should read --is--; line 51, "amimal" should read --aminal--. Column 2, line 7, equation 1, "+ $H_2$" should read --+ $H_2O$--; line 18, "animal" should read --aminal--. Column 3, line 17, equation 5, "H-C-R" should read --H-C-Ar--. Column 4, line 20, "aliphatic" should read --Aliphatic--.

Signed and Sealed this

Fourteenth Day of April 1981

[SEAL]

Attest:

RENE D. TEGTMEYER

*Attesting Officer*     *Acting Commissioner of Patents and Trademarks*